United States Patent [19]

Kodera

[11] 4,396,582
[45] Aug. 2, 1983

[54] METHOD AND APPARATUS FOR STERILIZING FOOD PACKAGES OR THE LIKE

[75] Inventor: Tokio Kodera, Fuchu, Japan

[73] Assignee: Dai Nippon Insatsu Kabushiki Kaisha, Tokyo, Japan

[21] Appl. No.: 247,209

[22] Filed: Mar. 24, 1981

[30] Foreign Application Priority Data

| Mar. 31, 1980 [JP] | Japan | 55-41832 |
| May 7, 1980 [JP] | Japan | 55-60281 |
| Sep. 30, 1980 [JP] | Japan | 55-136158 |
| Sep. 30, 1980 [JP] | Japan | 55-136159 |

[51] Int. Cl.³ .................................................. A61L 2/00
[52] U.S. Cl. .................................... 422/300; 53/167; 422/24; 422/31
[58] Field of Search ............... 426/24, 12, 399, 401, 426/234, 248; 53/167, 425, 426, 22, 24; 422/28, 31, 300, 186, 24

[56] References Cited

U.S. PATENT DOCUMENTS

| 1,723,603 | 8/1929 | Chesney | 426/248 |
| 3,583,132 | 6/1971 | Doyen | 53/167 |
| 3,692,468 | 9/1972 | Loliger et al. | 53/167 |
| 3,929,409 | 12/1975 | Buchner et al. | 422/300 |
| 3,947,249 | 3/1976 | Egger | 53/167 |
| 4,152,464 | 5/1979 | Brody et al. | 53/167 |
| 4,175,140 | 11/1979 | Bachman et al. | 426/399 |
| 4,289,728 | 9/1981 | Peel et al. | 422/24 |

FOREIGN PATENT DOCUMENTS

| 40-16061 | 4/1965 | Japan | 426/234 |

*Primary Examiner*—Bernard Nozick
*Attorney, Agent, or Firm*—Parkhurst & Oliff

[57] ABSTRACT

An object such as a food packaging material is sterilized first by immersion in a nontoxic sterilizing liquid and then by exposure to ultraviolet irradiation. The sterilizing liquid can be either an organic acid solution or hot water. Alternatively, the object is simultaneously treated with both sterilizing agents, by being irradiated with ultraviolet rays while being dipped in the sterilizing liquid. The liquid is reconditioned, as by filtration and ultraviolet irradiation while being recirculated through a closed circuit. The apparatus is disclosed as adapted for the sterilization of a continuous strip of food packaging film.

8 Claims, 8 Drawing Figures

METHOD AND APPARATUS FOR STERILIZING FOOD PACKAGES OR THE LIKE

BACKGROUND OF THE INVENTION

This invention relates to the art of sterilization in general and, in particular, to a method of sterilizing food packaging materials, food packages, or comparable objects by dual agents. The invention also particularly concerns an apparatus for sterilizing, typically, a continuous strip of food packaging film in accordance with the inventive method.

Chemical sterilization and physical sterilization represent two broad categories into which there can be classified various known methods of destroying microbial life on and in an object such as food packages. Chemical sterilization involves the use of such chemical substances as ethylene oxide, propylene oxide, and hydrogen peroxide. The gases of the first named two compounds have good sterilizing effects and permit, as an additional advantage, easy application to completed packages. These gases are toxic, however, inviting an objection if not thoroughly removed from the packages after treatment. Hydrogen peroxide, on the other hand, has recently been reported to be a possible cause of cancer, and this has doomed its use as a sterilizer in the food processing or manufacturing industry.

Although a myriad of other known bactericidal or disinfectant chemicals do exist, each has some drawback or another, such as toxicity or low sterilizing ability. None is quite suitable for the sterilization of food packages.

Radiation sterilization means the irradiation of the object with gamma rays, ultraviolet radiation, etc. Gamma rays permeate plastics and so, like the above noted gases, can sterilize food packages of such material in their final phase of fabrication. This advantage is offset, however, by the fact that gamma rays impair the heat sealing strength of the irradiated material and, when applied to plastic films or the like, cause discoloration.

Ultraviolet rays are less hazardous to man, and therefore are easier to handle, than other forms of radiant energy. They also leave no residue on the irradiated object. However, ultraviolet radiation possesses the drawback of acting on exposed surfaces only; even dust particles on the irradiated surfaces shield the underlying surface portions from the rays, obstructing their complete sterilization.

As may have been understood from the foregoing consideration of the prior art, the conventional methods of sterilization all have one problem or another. None is self-sufficient for the sterilization of food packaging materials, food packages or like objects.

SUMMARY OF THE INVENTION

The present invention seeks to overcome the drawbacks inherent in each of the listed conventional sterilizing methods by making combined use of two complementary agents for the sterilization of food packages, among other objects. The packages to be treated may be in either blank, semifinished, or finished form. The invention also seeks to avoid the deterioration of the physical properties of the packages, or of the products to be contained therein, as a result of their sterilization.

Essentially, the invention is based upon the discovery that the combined use of some nontoxic sterilizing liquid and ultraviolet radiation can sterilize the object far more effectively than is possible with each agent alone. The sterilizing liquid can be either an organic acid solution or hot water, which are both absolutely nontoxic. Preferably heated to a temperature of about 65° C. or more, such a liquid can kill molds, yeasts, lactic acid bacteria, etc., besides being effective in removing dust and like solids from the object. Ultraviolet radiation, on the other hand, can destroy bacterial spores or the like that cannot be killed by the liquid.

Thus the method of this invention comprises the steps of treating the object to be sterilized with the sterilizing liquid and exposing the object to ultraviolet radiation. The object may either be first treated with the sterilizing liquid and then irradiated with ultraviolet rays or may be simultaneously subjected to both steps of sterilization. The ultraviolet irradiation of the object should not precede its treatment with the sterilizing liquid because, as has been mentioned, even dust particles on the object can shield the underlying surface portions from the rays. The sterilizing liquid will perform its intended functions to the full if reconditioned, either constantly or at intervals, by being recirculated through a closed reconditioning circuit equipped for both filtration and ultraviolet irradiation of the liquid.

The apparatus according to this invention is well adapted for the continuous sterilization of a strip of film for packaging foods. One preferred form of the apparatus comprises a sterilizing vessel containing either an organic acid solution or heated water, in which the film strip is dipped while being fed along a specific path, and a pair of ultraviolet lamps disposed downstream of the sterilizing vessel for irradiating the opposite surfaces of the pretreated strip. In another preferred embodiment of the invention, the sterilizing vessel has windows fitted with panes of quartz or like material that pass ultraviolet radiation. Ultraviolet lamps located outside the windows irradiate the strip being immersed in the liquid in the sterilizing vessel.

The above and other objects, features and advantages of this invention and the manner of attaining them will become more apparent, and the invention itself will best be understood, from the following description and appended claims, taken in connection with the attached drawings.

DETAILED DESCRIPTION OF THE INVENTION

Figure 1:
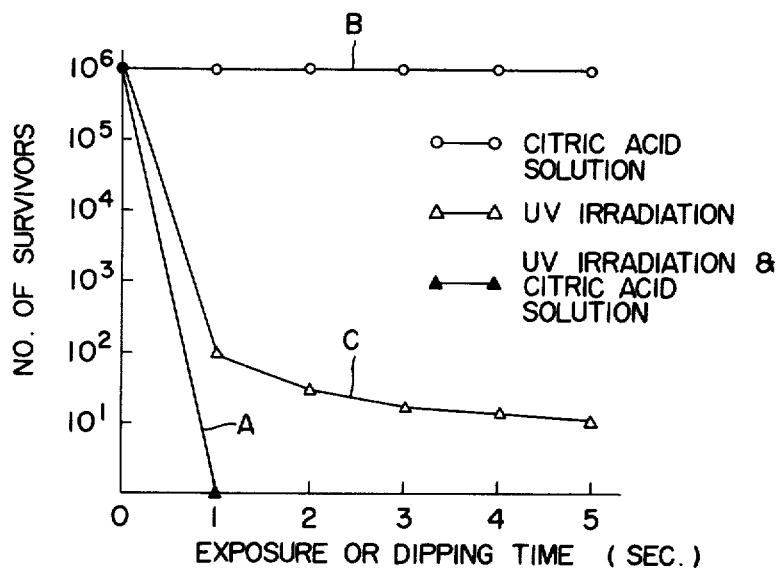
FIG. 1 is a graph plotting the survival rates of *Bacillus subtilis* spores treated in three different ways, namely, immersion in a solution of citric acid by way of an example of organic acids, exposure to ultraviolet radiation, and both.

As indicated in the foregoing summary, the present invention proposes the combined use of a nontoxic sterilizing liquid and ultraviolet radiation for the complete sterilization of food packages or the like. The object to be sterilized should first be immersed in, or otherwise placed in contact with, the sterilizing liquid and then irradiated with ultraviolet rays. This sequence should not be reversed. If desired, however, the object may be simultaneously treated with the sterilizing liquid and exposed to ultraviolet radiation. The sterilizing liquid can be either a solution of any of the organic acids set forth below or hot water.

The organic acids suitable for use in the practice of the inventive method include, but are not limited to, citric acid, glucono-delta-lactone gluconic acid, succinic acid, tartaric acid, lactic acid, acetic acid, fumaric acid, and malic acid. These organic acids are normally used in the form of aqueous solutions with a pH of not more than about three. The solutions should be heated to a temperature of about 65° C. or more for the best results.

The organic acids are particularly well suited for the sterilization of packages for acid foods or beverages, which are susceptible to attack by molds, yeasts, and lactic acid bacteria. The solutions of the organic acids can kill all these microorganisms. Further, the organic acid solutions do not affect the flavors of the acid foods filled into the treated packages, nor do they degrade the physical properties of the packages.

In order to confirm the sterilizing abilities of the organic acids, experiments were carried out as in the following, with citric acid taken as a representative of the organic acids. The object to be sterilized in these experiments was laminated food-packaging film consisting of polyethylene and polystyrene plies, cut into pieces about 100 cm² in size. Onto respective pieces of film were sprayed $10^6$ *Aspergillus nigers* as an example of mold-creating fungi, *Saccharomyces cerevisiae* as an example of yeasts, *Lactobacillus brevis* as an example of lactic acid bacteria, and $10^2$ *Bacillus subtilis* spores as an example of bacterial spores, a sufficient number of pieces of film bearing each of the microorganisms being thus prepared for the further processes and tests described below.

After having been dried, the test pieces prepared as described above were immersed in a 0.01 weight % aqueous solution of citric acid, with a pH of 2.6. The temperature of the citric acid solution was set at 45°, 50°, 60°, 65° and 70° C., and at each temperature the different test pieces were immersed in the solution for 5, 10, 15 and 30 seconds. The immersed test pieces were then dried and placed in a germfree nutrient media in order to culture the treated microorganisms. The nutrient media and other conditions of culture were as given in Table 1.

TABLE 1

| Microorganism | Culture Conditions Medium | Temp. °C. | Time hr |
|---|---|---|---|
| Aspergillus niger | Potato dextrose with agar | 25 | 72 |
| Saccharomyces cerevisiae | Potato dextrose with agar | 30 | 72 |
| Lactobacillus brevis | Tomato juice with agar | 35 | 48 |
| Bacillus subtilis | Usual bacteriological agar medium | 37 | 48 |

Table 2 summarizes the results of culturing the treated microorganisms under the foregoing conditions.

TABLE 2

| | | Results of Culture (O, dead; X, alive) Immersion Time, Sec. | | | |
|---|---|---|---|---|---|
| Microorganism | Solution Temp., °C. | 5 | 10 | 15 | 30 |
| Aspergillus niger | 45 | X | X | X | X |
| | 50 | X | X | X | X |
| | 60 | X | X | O | O |
| | 65 | O | O | O | O |
| | 70 | O | O | O | O |
| Saccharomyces cerevisiae | 45 | X | X | X | X |
| | 50 | X | X | X | O |
| | 60 | X | O | O | O |
| | 65 | O | O | O | O |
| | 70 | O | O | O | O |
| Lactobacillus brevis | 45 | X | X | X | X |
| | 50 | X | X | X | X |
| | 60 | X | X | X | X |
| | 65 | O | O | O | O |
| | 70 | O | O | O | O |
| Bacillus subtilis | 45 | X | X | X | X |
| | 50 | X | X | X | X |
| | 60 | X | X | X | X |
| | 65 | X | X | X | X |
| | 70 | X | X | X | X |

It will be observed from Table 2 that the citric acid solution at temperatures of 65° C. or more can destroy all but the bacterial spores of the tested four kinds of microorganisms if they are immersed in the solution for at least five seconds.

Further experiments were conducted to ascertain the abilities of packages sterilized with an organic acid solution to extend the shelf life of some acid beverages subsequently placed therein. Laminar polyethylene-polystyrene, 250-milliliter pouches were first sterilized by immersion in a citric acid solution, under the above specified conditions in accordance with the invention. Heat-sterilized in the usual manner, orange juice and apple juice were each filled into 100 pouches treated as described above, at a temperature of 15° C. and in a manner well calculated to avoid contamination of the products during such filling. The filled pouches were sealed closed. By way of comparison, heat-sterilized orange juice and apple juice were each charged into 100 untreated pouches of the same make in a like manner, and these pouches were also sealed closed.

The filled pouches, both sterilized and unsterilized, were all allowed to stand for one month at an ambient temperature of 30° C. The orange and apple juices in the unsterilized pouches were all found to be spoiled upon the elapse of the one-month period. The juices in the sterilized pouches were not spoiled at all, retaining their tastes and freshness.

As had been demonstrated by the foregoing results of experimentation, the solution of citric acid representative of the various adoptable organic acids is lethal, at temperatures above about 65° C., to molds, yeasts, and lactic acid bacteria, but not to bacterial spores. The surviving bacterial spores can be killed by the subsequent, or concurrent, step of ultraviolet sterilization, as will be later explained in more detail.

In the practice of the inventive method, the organic acid solution in use should be reconditioned, either constantly or at intervals, for utmost sterilization of any desired object. The solution can be reconditioned by either filtration, ultraviolet irradiation, or both, while being recirculated through a closed circuit. Thus reconditioned, the solution will kill microorganisms on, and remove dust from, the object to a greater extent than when not reconditioned, as has been evidenced by the experiments set forth hereinbelow.

A citric acid solution was also employed in these experiments for the sterilization of a strip of laminated polyethylene-polystyrene film. One hundred *Bacillus subtilis*, $10^6$ *Aspergillus nigers*, and $10^6$ *Saccharomyces cerevisiaes* were each sprayed onto respective areas of 100 cm² of the polyethylene-ply surface of the film strip. After having been dried, the film strip was passed through the citric acid solution in a vessel. In one phase of the experiment, the solution was recirculated through a closed reconditioning circuit equipped with facilities for filtration, ultraviolet irradiation, or both, while, in another phase, the solution was not recirculated. The capacity of the vessel was 50 liters, and the solution was recirculated at a rate of one liter per minute. The reconditioning circuit had two bacteriological filters disposed one after the other. The upstream one of these filters was Pall Filter MCS 1001RK (trademark) manufactured by Pall Trinitymicro Corp., of the United States, which is capable of 100% removal of solid particles 18 microns or more in size. The downstream filter was Pall Filter Ultipor AR (trademark) also manufactured by Pall Trinity-micro Corp., which is capable of 100% removal of solid particles 0.2 micron or more in size. For the ultraviolet irradiation of the solution, a model UV-C13 ultraviolet lamp manufactured by Brown Boveri Co., of Switzerland was employed. Table 3 represents the results obtained after two hours of operation under these conditions.

TABLE 3

Effects of Reconditioning

| Contaminant | Reconditioning Method | | | |
|---|---|---|---|---|
| | UV Radiation | Filtration | UV Radiation & Filtration | None |
| Dust particles above 10μ (per 100 cm² of film surface) | 1-2 | 0 | 0 | 1-2 |
| Dust particles above 10μ (per 100 cc of sterilizing solution) | 5-10 | 1 | 1 | 5-10 |
| *B. subtilis* (per 100 cm² of film surface) | 0 | 0 | 0 | 50-80 |
| *B. subtilis* (per 100 cc of sterilizing solution) | 0 | 0 | 0 | 10-20 |

Table 3 indicates that the constant reconditioning of the organic acid solution by filtration, ultraviolet radiation, or both makes possible complete removal of *Bacillus subtilis* both from the film strip and from the solution. The reconditioning of the solution by ultraviolet radiation only is not recommended, however, because it is unable to remove dust particles. The complete removal of dust from the object is a prerequisite for its most effective sterilization by subsequent or simultaneous exposure to ultraviolet rays.

The invention also suggests the use of hot water for the sterilization of the object, either before or at the same time with its exposure to ultraviolet radiation. The following experiments will illustrate the sterilizing effects of hot water.

*Aspergillus niger* and *Bacillus subtilis* spores were treated with water heated to the temperatures of 45°, 50°, 60°, 65°, 70° and 100° C., at each of which the microorganisms were immersed in the water for 5, 10 and 30 seconds. The thus-treated microorganisms were then cultured in a prepared nutrient media, and under other conditions, given in Table 4.

TABLE 4

| | Culture Conditions | | |
|---|---|---|---|
| Microorganism | Medium | Temp. °C. | Time hr |
| *Aspergillus niger* | Potato dextrose with agar | 25 | 72 |
| *Bacillus subtilis* spores | Potato dextrose with agar | 35 | 72 |

Table 5 represents the results of the culture under the conditions of Table 4.

TABLE 5

| | Results of Culture | | |
|---|---|---|---|
| | Water | (O, dead; X, alive) Immersion Time, Sec. | | |
| Microorganism | Temp., °C. | 5 | 10 | 30 |
| *Aspergillus niger* | 45 | X | X | X |
| | 50 | X | X | X |
| | 60 | X | X | O |
| | 65 | O | O | O |
| | 70 | O | O | O |
| | 100 | O | O | O |
| *Bacillus subtilis* spores | 45 | X | X | X |
| | 50 | X | X | X |
| | 60 | X | X | X |
| | 65 | X | X | X |
| | 70 | X | X | X |
| | 100 | X | X | X |

It is clear from Table 5 that water heated to a temperature of 65° C. or more can kill *Aspergillus niger* immersed therein for at least five seconds, but not *Bacillus subtilis* spores. Hot water is also known to destroy other molds, yeasts, and lactic acid bacteria. *Bacillus subtilis* and other heat-resistant bacteria can be killed by ultraviolet radiation. The sterilizing capacity of ultraviolet radiation will be enhanced as the hot water washes the object clean of dust and other foreign matter that have been adhering to the object electrostatically. It is to be understood that the object need not necessarily be simply immersed in heated water or in an organic acid solution but may be moved therein or therethrough, or the sterilizing liquid may be sprayed onto, made to flow in contact with, or otherwise applied to, the object.

As has been stated in conjunction with the organic acid solutions, hot water should also be reconditioned by being recirculated through a reconditioning circuit for the best results. Either filtration, ultraviolet irradiation, or both may be used for the reconditioning of hot water.

Reference is directed to Table 6, below, for the sterilizing performance of ultraviolet radiation. Tabulated there are the doses of ultraviolet rays needed to kill 99.9% of the listed microorganisms on a nutrient media.

TABLE 6

Effects of Ultraviolet Radiation

| Microorganism | UV Radiation Dose $\mu W \cdot min/cm^2$ |
| --- | --- |
| E. coli | 90 |
| Staphylococcus aureus | 155 |
| Saccharomyces cerevi | 314 |
| Pichia miyagi | 640 |
| Penicillum roqueforti | 440 |
| Aspergillus niger | 4400 |
| Rhizopus nigricans | 3700 |
| Bacillus subtilis | 360 |
| Bacillus subtilis spore | 554 |

Table 6 reveals that ultraviolet radiation works well with heat-resistant bacterial spores such as those of *Bacillus subtilis*, but not so much with mold-creating fungi such as *Aspergillus niger*. The sterilizing effectiveness of ultraviolet radiation is known to lessen, moreover, if the irradiated surfaces carry dust or the like and if there are too many microorganisms to be killed.

From the foregoing considerations and results of experimentation, the present invention advocates the sterilization of food packages or the like by means of the two complementary agents, the nontoxic sterilizing liquid, such as an organic acid solution or hot water, and ultraviolet radiation. In order to derive the full benefits from the sterilizing agents, and to cancel their drawbacks, the object should first be immersed in or otherwise treated with the sterilizing liquid and then exposed to ultraviolet radiation. Satisfactory results will be obtained, however, if the object is simultaneously treated with both agents.

Preferably, the object should be freed of dust and similar foreign matter, as far as possible, prior to its introduction into the sterilizing liquid and exposure to ultraviolet rays. Dust removal from the object is possible either mechanically, as by brushes, or pneumatically, as by application of pressurized air streams. Such dust removal will redound to the more thorough sterilization of the object by the subsequent steps of treatment with the sterilizing liquid and ultraviolet rays.

According to another incidental feature of the method according to the invention, the object is heated, as by infrared radiation, either before, between, or after the noted steps of sterilization. The object should preferably be heated in an atmosphere of increased humidity, in order to destroy *Aspergillus niger* or like molds that are highly resistive to ultraviolet radiation. Such molds will die if held at a temperature of 70° C. for five seconds or so under high humidity.

Given below are some Examples of the inventive method as adapted for the sterilization of polystyrene film used for packaging foods.

EXAMPLE I

Circular pieces of polystyrene film, each with a diameter of 90 mm, were each sprayed with $10^6$ *Bacillus subtilis* spores. After having been dried, these test pieces were first dipped for varying lengths of time in a germfree aqueous solution of citric acid having a pH of 3.0 and heated to a temperature of 65° C. Thereafter the test pieces were exposed to ultraviolet radiation at a distance of 20 mm from its source (the model UV-C13 ultraviolet lamp by Brown Boveri Co.), also for varying lengths of time. The thus-treated test pieces were then placed in sterilized laboratory dishes into which a germfree culture medium was poured, prepared by gelling meat extract with agar, in order to check the test pieces for sterility.

The results were as represented by the curve A in the graph of FIG. 1. The curve indicates that the ultraviolet irradiation of the test pieces for one second, following their immersion in the citric acid solution for 10 seconds, sufficed to destroy all the *Bacillus subtilis* spores.

By way of comparison, similar test pieces were sterilized by immersion in a citric acid solution, also with a pH of 3.0 and a temperature of 65° C., and by exposure to ultraviolet radiation, respectively. The sterility of the test pieces treated by these conventional methods was checked by the same method as above. As shown by the curve B in FIG. 1, the citric acid solution by itself could kill no *Bacillus subtilis* spores. Ultraviolet radiation, on the other hand, was unable to destroy all the spores even when applied to the test pieces for five seconds, as exhibited by the curve C.

EXAMPLE II

Figure 2:
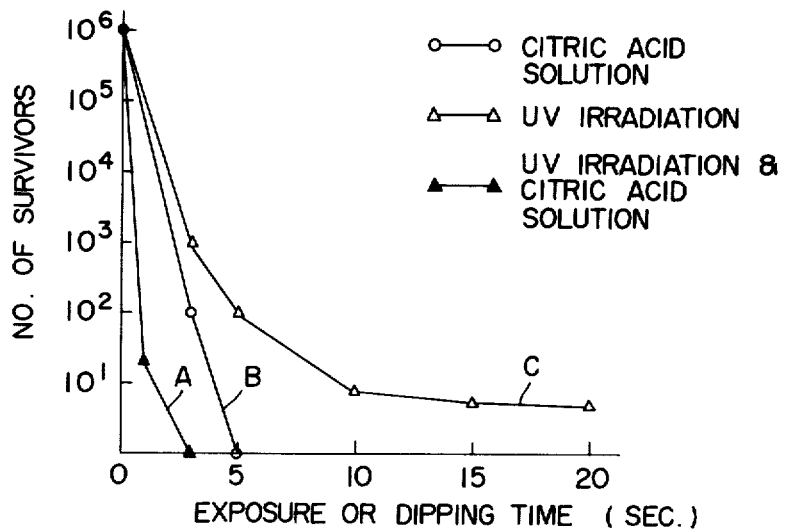
FIG. 2 is a graph plotting the survival rates of *Aspergillus niger* endospores also treated in the above three ways.

Each circular piece of polystyrene film, also with a diameter of 90 mm, was sprayed with $10^6$ *Aspergillus niger* endospores. After having been dried, the test pieces were immersed in a germfree citric acid solution having a pH of 3.0 and heated to a temperature of 65° C. and then were irradiated with the UV-C13 ultraviolet lamp at a distance of 20 mm. Subsequently placed in sterilized laboratory dishes, the test pieces were checked for sterility by pouring into the dishes a germfree culture medium in the form of potato dextrose gelled with agar. As represented by the curve A in the graph of FIG. 2, the ultraviolet irradiation of the test pieces for three seconds, after their immersion in the citric acid solution, proved sufficient to destroy all the *Aspergillus niger* endospores.

Similar test pieces were treated with the citric acid solution and with ultraviolet radiation, respectively, under the same conditions as above by way of comparison. The sterility of the thus-treated test pieces was checked by the above described method. The curve B in FIG. 2 demonstrates that the test pieces had to be immersed in the citric acid solution for five seconds to kill all the endospores. Ultraviolet radiation was unable to destroy all the endospores even when applied to the test pieces for 20 seconds, as indicated by the curve C.

EXAMPLE III

Each circular piece of polystyrene film with a diameter of 90 mm was sprayed with $10^6$ *Bacillus subtilis* spores. After having been dried, the test pieces were immersed in sterilized water heated to a temperature of 65° C. and then were irradiated with the UV-C13 ultraviolet lamp at a distance of 20 mm. The treated spores were cultured by the same method as above to ascertain the sterility of the test pieces. As indicated by the curve A in the graph of FIG. 3, it is apparent that the test pieces became sterile when exposed to ultraviolet radiation for five seconds after their immersion in the heated water for 10 seconds.

Figure 3:
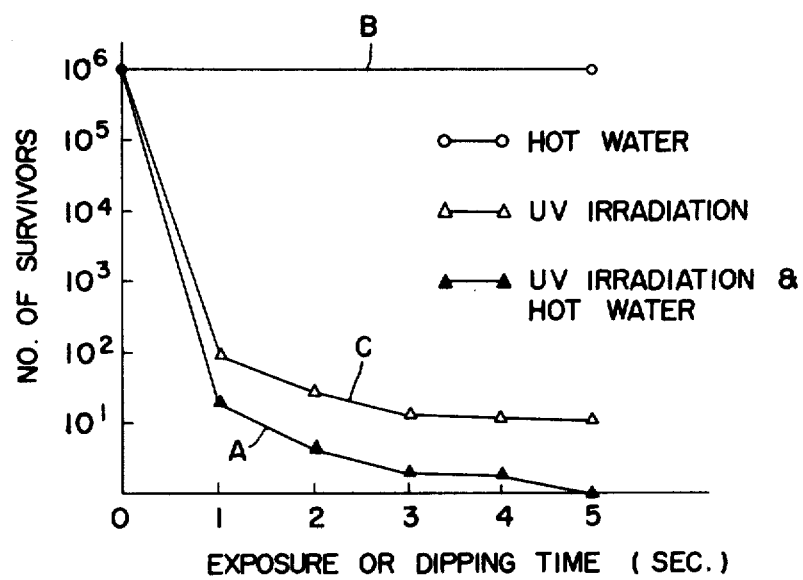
FIG. 3 is a graph plotting the survival rates of *Bacillus subtilis* spores treated by immersion in hot water, exposure to ultraviolet radiation, and both.

Similar test pieces were treated with only sterilized water heated to a temperature of 65° C. and were checked for sterility by the same method as above. The curve B in FIG. 3 shows that the hot water alone was utterly unable to kill the *Bacillus subtilis* spores. The curve C in FIG. 3 is the same as the curve C in FIG. 1, indicating that ultraviolet radiation by itself could not destroy all the spores in five seconds.

EXAMPLE IV

Each circular piece of polystyrene film with a diameter of 90 mm was sprayed with $10^6$ *Aspergillus niger* endospores. After having been dried, the test pieces were immersed in germfree water heated to a temperature of 65° C. and then were irradiated with the UV-C13 ultraviolet lamp at a distance of 20 mm. The thus-treated endospores were subcultured by the same method as above to ascertain the sterility of the test pieces. As represented by the curve A in the graph of FIG. 4, the test pieces were found to become sterile when immersed in hot water for two seconds and then exposed to ultraviolet radiation for one second.

Figure 4:
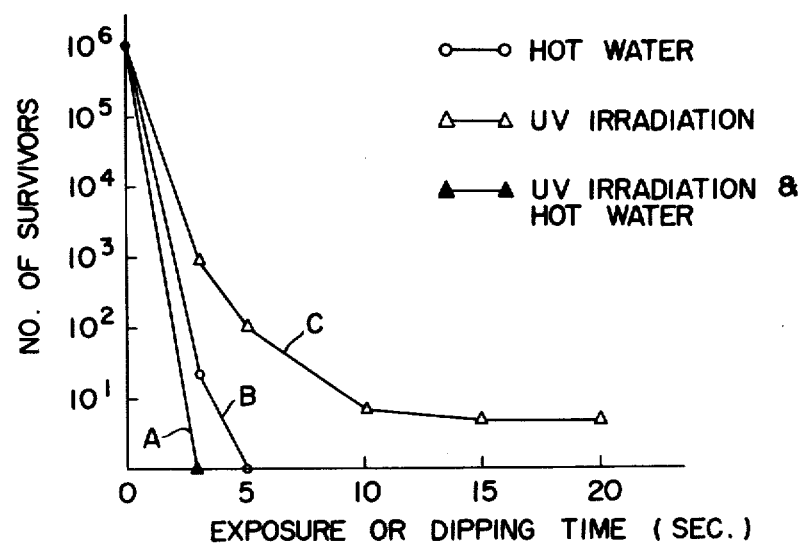
FIG. 4 is a graph plotting the survival rates of *Aspergillus niger* endospores also treated by immersion in hot water, exposure to ultraviolet radiation, and both.

Similar test pieces were sterilized only by immersion in water heated to a temperature of 65° C. and were checked for sterility by the same method as above. The curve B in FIG. 4 indicates that it took five seconds for the heated water to kill all the *Aspergillus niger* endospores. The curve C in FIG. 4 is the same as the curve C in FIG. 2, demonstrating that ultraviolet radiation alone could not destroy all the endospores in 20 seconds.

Preferred Form of Apparatus

Figure 5:
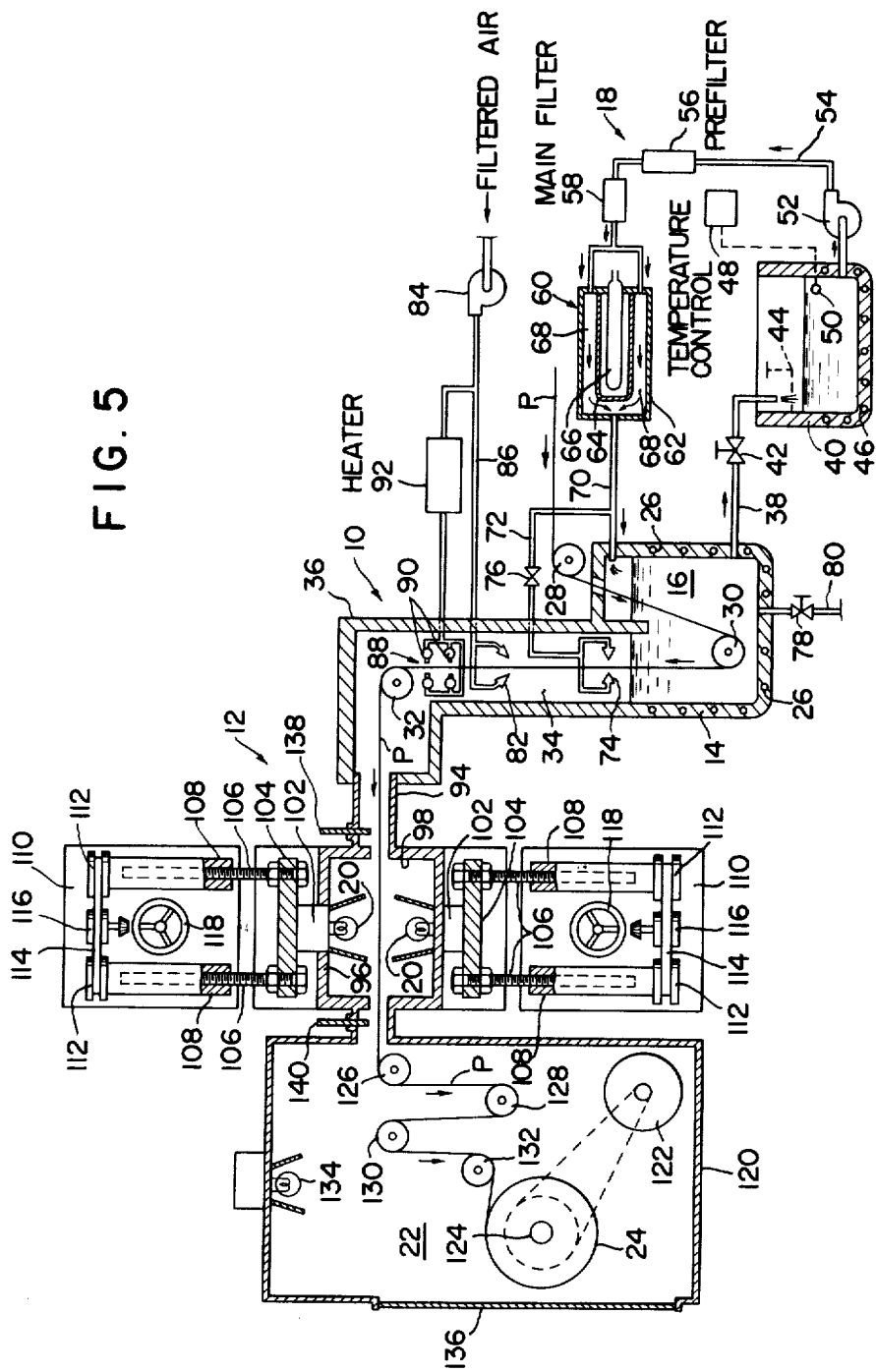
FIG. 5 is a diagrammatic representation of one example of the apparatus for sterilizing a continuous strip of food packaging film in accordance with the method of this invention.

FIG. 5 illustrates a preferred form of the apparatus for carrying out the above described method of this invention. The apparatus is herein shown adapted for the sterilization of a continuous strip P of polyethylene, polystyrene or like plastic film for packaging foods.

Broadly, the illustrated apparatus comprises a liquid sterilizer 10 and an ultraviolet sterilizer 12 for sterilizing the strip P of plastic film traveling therethrough in the direction of the arrows. The liquid sterilizer 10 includes a sterilizing vessel 14 containing a sterilizing liquid 16, which can be either an organic acid solution or hot water. The sterilizing vessel 14 forms a part of a closed circuit 18 for the recirculation and reconditioning of the liquid contained therein. The ultraviolet sterilizer 12 includes a pair of ultraviolet lamps 20 for irradiating the opposite surfaces of the strip P. Disposed downstream of the ultraviolet sterilizer 12, a takeup chamber 22 has a takeup spool 24 rotatably mounted therein for winding up the sterilized strip P.

The sterilizing vessel 14 has a built-in heater 26 for heating the liquid to a temperature of about 65° C. or more. Unwound from a payoff spool, not shown, the strip P enters the sterilizing vessel 14 as guided by a guide roll 28 and is dipped in the liquid 16 as it passes around and under another guide roll 30. The strip P leaves the sterilizing vessel 14 as it travels upwardly from the guide roll 30 to still another guide roll 32 through an airtightly sealed space 34 defined by an enclosure 36, which is shown to be integral with the vessel. Thus, as has been stated in connection with the method of this invention, the strip P is first sterilized by immersion in the organic acid solution or water heated to at least about 65° C.

The sterilizing vessel 14 communicates with an outlet circuit 38 included in a closed circuit 18 for the recirculation and reconditioning of the sterilizing liquid. The outlet conduit 38 opens into a storage vessel 40 via a valve 42. The storage vessel 40 has mounted therein a mesh filter 44, just under the exit end of the outlet conduit 38, for filtering the liquid as it issues therefrom. This storage vessel also has a built-in heater 46 for heating the liquid stored therein. Further, for maintaining the stored liquid at a constant temperature, the heater 46 is associated with a temperature control 48 having a temperature detector 50.

A pump 52 draws the sterilizing liquid from within the storage vessel 40 out into a conduit 54 having a prefilter 56 and a main filter 58, both of the bacteriological class, disposed one after the other. The prefilter 56 may take the form of the aforesaid Pall Filter MCS 1001RK by Pall Trinitymicro Corp., and the main filter 58 may take the form of Pall Filter Ultipore AR by the same corporation.

Disposed immediately downstream of the main filter 58 is an ultraviolet sterilizer 60 comprising a cylindrical enclosure 62, a cylindrical inner wall 64 mounted concentrically within the enclosure, and an ultraviolet-ray generator 66 mounted further inside the inner wall. The enclosure 62 and the inner wall 64 define in combination an annular passageway 68 for the liquid flowing from the main filter 58. The inner wall 64 is of quartz or like transparent material that passes the ultraviolet rays emitted by the generator 66, so that the liquid undergoes ultraviolet sterilization as it streams through the passageway 68.

Emerging from the ultraviolet sterilizer 60, the reconditioned liquid flows back into the sterilizing vessel 14 by way of a return conduit 70. This return conduit has a branch 72 projecting into the sealed space 34 on the outlet side of the sterilizing vessel 14 and terminating in a pair of nozzles 74. It is thus seen that part of the reconditioned liquid returns to the sterilizing vessel 14 after being sprayed onto the opposite surfaces of the strip P. The branch conduit 72 has a stop valve 76.

The aforementioned mesh filter 44, prefilter 56, main filter 58, and ultraviolet sterilizer 60 all function to recondition the liquid as it recirculates through the closed circuit 18, either constantly or at intervals. A discharge conduit 80 provided with a stop valve 78 is communicatively connected to the bottom of the sterilizing vessel 14.

In the sealed space 34, and just downstream of the nozzle pair 74, there are provided a pair of air knives 82 angled downwardly to direct thin, flat jets of filtered air against the opposite surfaces of the strip P. The air knife pair 82 communicates with a source 84 of pressurized air by way of a conduit 86.

A dryer 88 is also mounted in the sealed space 34, further downstream of the air knife pair 82. The dryer 88 has several nozzles 90, disposed on the opposite sides of the strip P, for application of filtered, heated streams of air thereto. The pressurized air source 84 also communicates with this dryer via a heater 92.

A passageway 94 airtightly communicates the enclosure 36 with a housing 96 of the ultraviolet sterilizer 12 defining an irradiation chamber 98, permitting the strip P to travel from the former to the latter. A pair of ultraviolet lamps 20 are disposed in the irradiation chamber 98, on the upper and lower sides of the strip P extending horizontally therethrough. Desirably, the distances of these ultraviolet lamps from the strip P should be adjustably variable in accordance with the degree of sterility of the strip treated by the liquid in the sterilizing vessel 14, and with the degree of degradation of its physical properties due to exposure to ultraviolet rays.

Toward this end each ultraviolet lamp 20 is mounted on a base 102 slidably extending through the housing 96 and affixed to a carriage 104 movable toward and away from the housing. Rigidly coupled to each carriage 104 are a pair of threaded rods 106 engaged in a pair of internally threaded sleeves 108, respectively. Each pair of sleeves 108 is rotatably mounted on some stationary part 110 while being locked against axial displacement. A driven pulley 112 is mounted on each sleeve 108 for simultaneous rotation therewith, and an endless belt 114 extends around the two driven pulleys on each sleeve pair and further over a drive pulley 116 disposed therethrough. Each drive pulley 116 is coupled to a handwheel 118 as via bevel gearing.

Thus, upon revolution of the two handwheels 118 in either direction, the sleeves 108 are belt driven to rotate in the corresponding direction, causing the axial displacement of the rods 106 threadedly engaged therein. The two ultraviolet lamps 20 are therefore adjustably moved toward or away from the strip P.

The irradiation chamber 98 is in open communication with the takeup chamber 22 defined by a housing 120. The takeup spool 24 in this takeup chamber is driven by a motor drive unit 122 for rotation on a shaft 124. As the motor drive unit 122 is set in rotation, the takeup spool 24 winds up the sterilized strip P traveling over four guide rolls 126, 128, 130 and 132 from the ultraviolet sterilizer 12. An additional ultraviolet lamp 134 is mounted on the ceiling of the housing 120 to maintain the takeup chamber 22 in a germfree state. The housing 120 has a door 136 for the withdrawal of the roll of sterilized strip P from the takeup chamber 22.

Two shield plates 138 and 140 are disposed just upstream and downstream, respectively, of the irradiation chamber 98 for vertical displacement. These shield plates serve to minimize the influx of the airborne droplets of the sterilizing liquid into and out of the irradiation chamber 98.

For sterilizing the continuous strip P of plastic film by the apparatus of FIG. 5, the strip may first be threaded through the apparatus as shown. Then the heaters 26 and 46 are set working, the ultraviolet lamps 20, 66 and 134 are lit, and the motor drive unit 122 is set into rotation. Drawn through the apparatus by the revolving takeup spool 24, the strip P is first dipped in the heated water or organic acid solution 16 in the sterilizing vessel 14 thereby to be sterilized and freed of dust and like foreign matter. The sterilizing liquid itself must be free of microorganisms and other contaminants throughout the progress of sterilizing operation, so that the liquid is recirculated through the reconditioning circuit 18 in the following manner.

As the valve 42 on the outlet conduit 38 is opened, the liquid flows from the sterilizing vessel 14 into the storage vessel 40. In thus flowing into the storage vessel, the liquid passes the mesh filter 44, to be freed of relatively coarse solids. The liquid is subsequently drawn out of the storage vessel 40 by the pump 52 and forced through the prefilter 56 and then through the main filter 58. These filters separate microorganisms from the liquid. After the filtration sterilization by the two successive filters 56 and 58, the liquid enters the ultraviolet sterilizer 60, where the microorganisms that may still persist in the liquid are all destroyed by ultraviolet irradiation. Thus thoroughly reconditioned, both by filtration and irradiation, the liquid returns to the sterilizing vessel 14 for reuse.

The three filters 44, 56 and 58 can normally separate all the microorganisms and other contaminants from the sterilizing liquid. The provision of the ultraviolet sterilizer 60 is therefore not of absolute necessity.

The valve 76 on the branch 72 of the return conduit 70 may be opened as required for spraying the reconditioned liquid onto both surfaces of the strip P from the pair of nozzles 74. The strip P emerging from the sterilizing vessel 14 may carry bubbles thereon, and such bubblecovered parts of the strip may not have been sterilized by the liquid in the vessel. The spraying of the reconditioned liquid onto the strip serves to remove the bubbles and sterilize the thus-exposed surface portions thereof, besides being effective in washing the strip clean of dust particles or the like. The valve 78 on the discharge conduit 80 may also be opened periodically to discharge the dead microorganisms, dust and other foreign matter that will accumulate on the bottom of the sterilizing vessel 14.

The pressurized air source 84 is in constant operation to deliver air under pressure to the pair of air knives 82 and, via the heater 92, to the dryer 88. The air knife pair 82 functions to remove the liquid from both surfaces of the strip P, and the dryer 88 to dry the strip subsequently.

Passing over the guide roll 32, the dried strip P enters the irradiation chamber 98 of the ultraviolet sterilizer 12. In this irradiation chamber the strip P undergoes ultraviolet sterilization by the pair of lamps 20 lying on its opposite sides. The distances of these ultraviolet lamps from the strip can be adjustably varied as aforesaid by turning the handwheels 118. Thus sterilized, the strip P travels into the takeup chamber 22 to be wound on the takeup spool 24.

Figure 6:
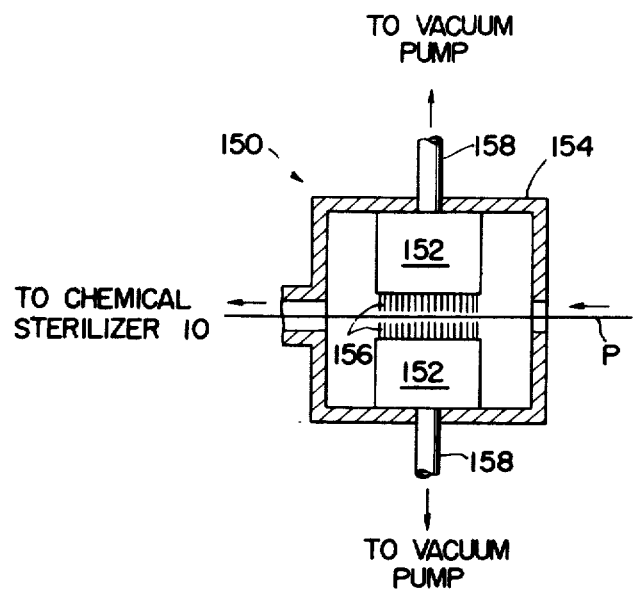
FIG. 6 is a diagrammatic, vertical sectional view of a dust remover which can be incorporated in the apparatus of FIG. 5.

FIG. 6 shows an example of dust remover 150 that can be incorporated in the apparatus of FIG. 5 as required or desired. Intended to be positioned upstream of the liquid sterilizer 10, the exemplified dust remover 150 takes the form of a vacuum cleaner comprising a pair of suction boxes 152 mounted within a housing 154 and disposed on the opposite sides of the strip P of plastic film, and a pair of brushes 156 mounted on the respective suction boxes for relative sliding contact with the opposite surfaces of the strip. The suction boxes 152 communicate with a vacuum pump by way of conduits 158.

Usually the strip P to be sterilized has dust and other solids electrostatically attached thereto. Although such foreign matter can be removed by the liquid sterilizer 10, its previous separation by the dust remover 150 is desirable in some instances. As the strip P travels through the dust remover 150, the pair of brushes 156 separate the solids from its surfaces, which are then drawn into the pair of suction boxes 152 for discharge. It is also possible to remove dust from the strip by application of air jets.

Figure 7:
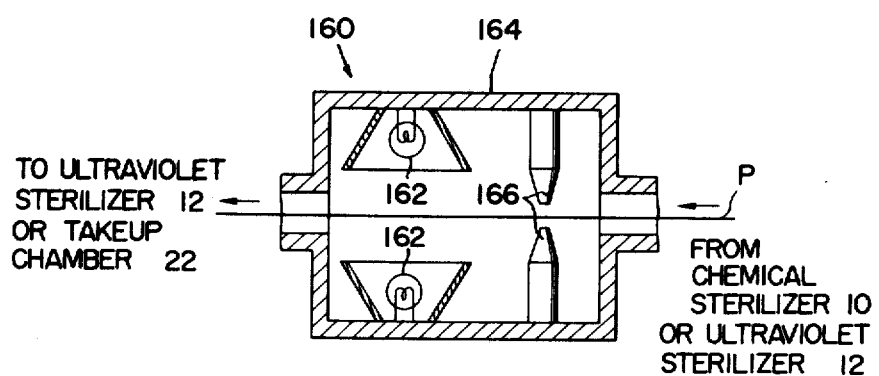
FIG. 7 is a similar view of a heater which can also be incorporated in the apparatus of FIG. 5.

In FIG. 7 is illustrated an example of heater 160 that can also be incorporated in the apparatus of FIG. 5 for destorying molds, in particular, on the strip P, which are highly resistive to ultraviolet radiation. Placed either upstream or downstream of the ultraviolet sterilizer 12, the heater 160 comprises a pair of infrared lamps 162 mounted within a housing 164 and arranged to irradiate the opposite surfaces of the strip passing therethrough. The surfaces of the strip should be moistened for the best results, as by a pair of ultrasonic humidifiers 166. Molds on the moistened surfaces of the strip will die if they are heated to and held at a temperature of 70° C. for five seconds or so.

Alternative Form

Figure 8:
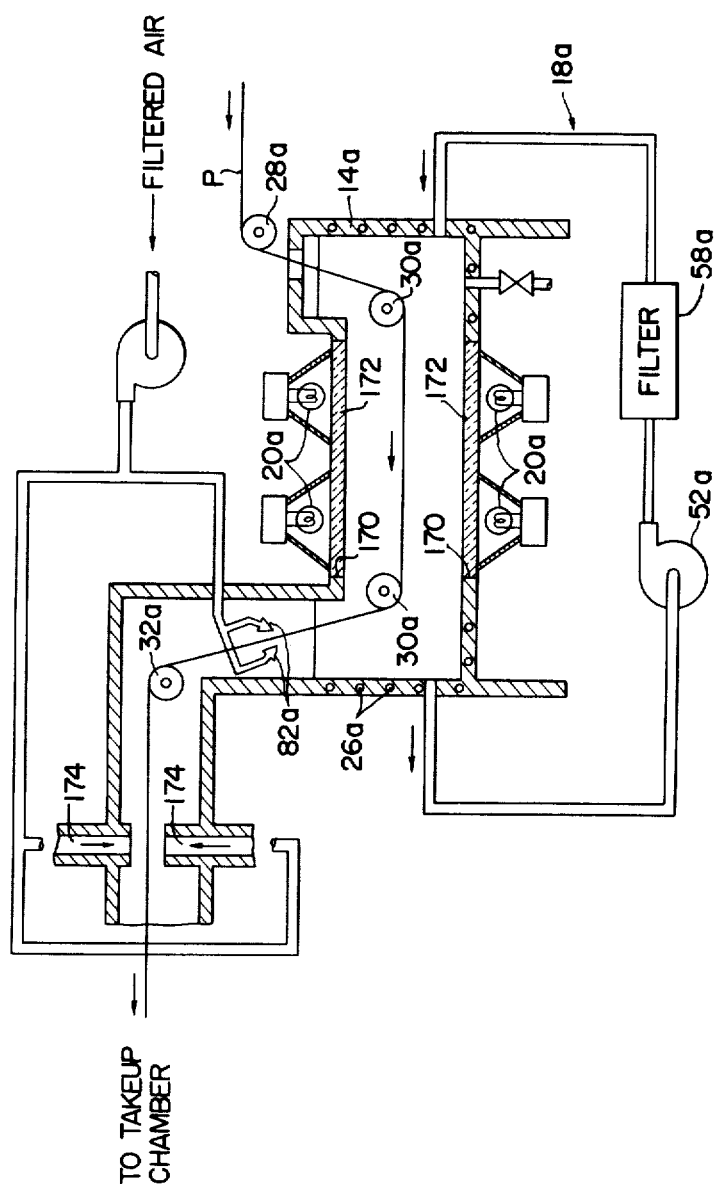
FIG. 8 is a partial, diagrammatic representation of an alternative form of the apparatus according to the invention.

It has been stated in relation with the inventive method that the object to be sterilized can be simultaneously processed with both the sterilizing liquid and ultraviolet radiation. The apparatus of FIG. 8 is designed on this principle, also as adapted for the continuous sterilization of a strip of food packaging film.

The apparatus includes a sterilizing vessel 14a containing a sterilizing liquid such as an organic acid solution or water, which is heated by a heater 26a. The strip P of film is dipped in the liquid as it advances through the apparatus as guided by four guide rolls 28a, 30a and 32a. The sterilizing vessel has a pair of windows 170 located on the opposite (upper and lower) sides of the strip P traveling therethrough. Each window is fitted with a pane 172 of quartz or like material that passes ultraviolet rays.

Mounted outside each quartz windowpane 172 are two ultraviolet lamps 20a arranged along the path of the strip P in the sterilizing vessel 14a. The ultraviolet lamps irradiate the surfaces of the strip P through the quartz windowpanes 172 and the liquid in the sterilizing vessel. Only one or more than two ultraviolet lamps could of course be provided outside each window, depending upon such factors as the intensity of radiation produced by each lamp, the distance of each lamp from the strip P, and the traveling speed of the strip. It will also be seen that this apparatus could be equipped with means for adjustably varying the distances of the ultraviolet lamps from the strip P, as in the case of those shown in FIG. 5.

The sterilizing vessel 14a forms a part of a closed circuit 18a for the recirculation and reconditioning of the sterilizing liquid. A pump 52a forces the liquid through the circiuit. It will be noted that the configuration of this reconditioning circuit is much simpler than that shown in FIG. 5, including only one bacteriological filter 58a. The single filter, well chosen, will remove microorganisms and other solids from the liquid to a practically acceptable degree.

Treated with both the sterilizing liquid and ultraviolet radiation at the same time, the strip P emerges from the sterilizing vessel 14a and receives air jets from a pair of air knives 82a for removal of the liquid therefrom. The strip is subsequently dried by streams of filtered air applied from a pair of air inlets 174. The drying air may be heated as in the preceding embodiment. Directed into a takeup chamber such as the one shown at 22 in FIG. 5, the dried strip is wound on a spool.

What is claimed is:

1. An apparatus for sterilizing an object such as food packaging material or a food package, comprising means for feeding the object along a prescribed path, a sterilizing vessel in the prescribed path for containing a sterilizing liquid heated to at least about 65° C., the object being immersed in the sterilizing liquid in the sterilizing vessel while being fed along the prescribed path, said sterilizing vessel having at least one window closed with a sheet of material that passes ultraviolet rays, and means for irradiating the object with ultraviolet rays through said window simultaneous with or after the immersion in sterilizing liquid while the object is being fed along the prescribed path.

2. An apparatus for sterilizing an object such as food packaging material or a food package, comprising:
means for feeding the object along a prescribed path;
a sterilizing vessel in the prescribed path, for containing a sterilizing liquid, the object being immersed in the sterilizing liquid in the sterilizing vessel while being fed along the prescribed path; and
means for irradiating the object with ultraviolet rays while the object is being fed along the prescribed path, said means for irradiating comprising at least two ultraviolet lamps disposed on opposite sides of the prescribed path and means for adjustably moving the ultraviolet lamps toward and away from the prescribed path.

3. An apparatus for sterilizing an object such as food packaging material or a food package, comprising:
means for feeding the object along a prescribed path;
a sterilizing vessel in the prescribed path for containing a sterilizing liquid, the object being immersed in the sterilizing liquid in the sterilizing vessel while being fed along the prescribed path;
means for irradiating the object with ultraviolet rays while the object is being fed along the prescribed path;
means for recirculating the sterilizing liquid through a closed circuit, of which the sterilizing vessel forms a part; and
means in the closed circuit for reconditioning the sterilizing liquid, said reconditioning means comprising means for filtering the sterilizing liquid, said filtering means comprising two bacteriological filters of different pore sizes disposed one after the other.

4. The sterilizing apparatus according to claim 3, wherein a storage vessel is disposed between the sterilizing vessel and the bacteriological filters, and wherein the filtering means further comprises a mesh filter mounted in the storage vessel for filtering the sterilizing liquid as the same flows into the storage vessel.

5. An apparatus for sterilizing an object such as food packaging material or a food package, comprising:
means for feeding the object along a prescribed path;
a sterilizing vessel in the prescribed path for containing a sterilizing liquid, the object being immersed in the sterilizing liquid in the sterilizing vessel while being fed along the prescribed path;
means for irradiating the object with ultraviolet rays while the object is being fed along the prescribed path;
means for recirculating the sterilizing liquid through a closed circuit, of which the sterilizing vessel forms a part; and
means in the closed circuit for reconditioning the sterilizing liquid, said reconditioning means further comprising means for exposing the sterilizing liquid to ultraviolet radiation.

6. The sterilizing apparatus according to claim 5, wherein the exposing means comprises means defining a passageway for the sterilizing liquid and having a wall made of a material that passes ultraviolet rays, and a source of ultraviolet radiation for irradiating the sterilizing liquid through the wall.

7. The sterilizing apparatus according to any one of claims 2, 3 or 5, wherein the sterilizing vessel is located upstream of the irradiating means with respect to the direction in which the object is fed along the prescribed path.

8. The sterilizing apparatus according to any one of claims 2, 3 or 5, wherein the sterilizing vessel has at least one window closed with a sheet of material that passes ultraviolet rays, and wherein the irradiating means irradiates the object through the window.

* * * * *